United States Patent
McNair (10) Patent No.: US 10,420,486 B1
(45) Date of Patent: Sep. 24, 2019

(54) PROMOTING POSITIVE ACTIVITY PATTERNS

(71) Applicant: Cerner Innovation, Inc., Lenexa, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 748 days.

(21) Appl. No.: 13/751,961

(22) Filed: Jan. 28, 2013

Related U.S. Application Data (60) Provisional application No. 61/591,515, filed on Jan. 27, 2012.

(51) Int. Cl.
*A61B 5/11* (2006.01)
*A61B 5/00* (2006.01)

(52) U.S. Cl.
CPC .............. *A61B 5/1118* (2013.01); *A61B 5/72* (2013.01); *A61B 5/742* (2013.01); *A61B 5/7405* (2013.01); *A61B 5/7455* (2013.01)

(58) Field of Classification Search
CPC ...... A61B 5/4528; A61B 5/1071; A61B 5/103
USPC .................................................. 600/587, 595
See application file for complete search history.

(56) References Cited

U.S. PATENT DOCUMENTS

| | | | | |
|---|---|---|---|---|
| 4,407,297 | A * | 10/1983 | Croslin .............. | A61B 5/02225 600/494 |
| 6,997,882 | B1 * | 2/2006 | Parker et al. ................. | 600/534 |
| 2005/0115561 | A1 * | 6/2005 | Stahmann et al. ........ | 128/200.24 |
| 2007/0146116 | A1 * | 6/2007 | Kimbrell ................ | A61B 5/681 340/5.52 |
| 2008/0010352 | A1 * | 1/2008 | Donoho ................. | G06Q 30/02 709/206 |
| 2009/0099467 | A1 * | 4/2009 | Toren-Herrinton et al. ................. 600/508 |
| 2009/0240155 | A1 * | 9/2009 | Nakayama ......... | A61B 5/02416 600/500 |
| 2009/0247910 | A1 * | 10/2009 | Klapper ........................ | 600/595 |
| 2011/0144543 | A1 * | 6/2011 | Tsuzuki ................ | A61B 5/1114 600/595 |

(Continued)

OTHER PUBLICATIONS

First Action Interview Preinterview Communication dated Oct. 11, 2016 in U.S. Appl. No. 14/585,930, 3 pages.

*Primary Examiner* — Daniel L Cerioni
(74) *Attorney, Agent, or Firm* — Shook, Hardy and Bacon, L.L.P.

(57) ABSTRACT

Methods, computer systems, and computer readable media are provided for promoting positive activity patterns for users and facilitate long-term adherence to the activity patterns, such as by providing alerts or electronic reminders to ambulate in a fashion that is responsive to an individual's actual activity patterns and behaviors and compatible with routine activities in the workplace and home. In particular, embodiments of the present invention are directed to (1) measuring physical activity patterns during the waking hours of a human, and in some embodiments continuously measuring these activity patterns; (2) automatically ascertaining whether the patterns exhibit sufficient frequency and variability of activity such as confers certain health benefits; and (3) if the patterns do not manifest such features, to adaptively provide sensible reminders at irregular within-day intervals such as are likely to establish healthy patterns of ambulation and other light activity.

19 Claims, 4 Drawing Sheets

(56) References Cited

U.S. PATENT DOCUMENTS

| | | | |
|---|---|---|---|
| 2011/0205051 A1* | 8/2011 | Katingari | A61B 5/0006 340/539.12 |
| 2011/0221569 A1* | 9/2011 | Hamel | A61B 5/0031 340/9.1 |
| 2012/0330109 A1* | 12/2012 | Tran | 600/301 |
| 2013/0012836 A1* | 1/2013 | Crespo Veiga | A61B 5/7221 600/595 |

* cited by examiner

PROMOTING POSITIVE ACTIVITY PATTERNS

CROSS-REFERENCE TO RELATED APPLICATIONS

This application claims the benefits of U.S. Provisional Application No. 61/591,515, titled "Randomized Reminding For Promoting Positive Activity Patterns," filed Jan. 27, 2012, which is hereby expressly incorporated by reference in its entirety.

INTRODUCTION

A major goal of industrialized Western societies is to reduce the prevalence of overweight and obesity and interrelated comorbid chronic health conditions. The burden of diabetes is increasing worldwide, indicating an urgent need to find the best standard for diabetes care. There is a close relationship between obesity and Type 2 diabetes: 90% of individuals with diabetes are overweight or obese. The basic treatment is weight loss, physical activity, and diet. However, research indicates that only a very small portion of weight lost is directly attributable to associated caloric expenditures, which tend to be especially low in obese and deconditioned individuals initiating exercise.

Exercise is a type of physical activity that is planned and structured. But there are non-exercise, unplanned forms of activity as well, such as intermittent walking and stair-climbing that are incidental to other daily activities, intermittent rising and sitting down, intermittent stretching, and so forth. It is proposed that all activity-induced changes in dynamic gene expression and neuroendocrine physiology contribute to the statistical association between physical activity, psychological state, metabolic state, and weight loss. It is possible that exercise- and non-exercise activity-induced improvements in adherence to exercise prescriptions are related to increased feelings of ability to control one's own behavior. Biochemical theories suggest that associated changes in endorphin, serotonin, and norepinephrine levels induce improvements; thus, there would be a dose-response effect (i.e., more exercise—more reduction in depression, more adherence, etc.). Conversely, behavioral theories suggest that simply participating in a program of physical activity fosters self-efficacy to manage one's self through barriers that lead to a generalized sense of well-being and improved adherence. Studies have supported both positions.

Many social and psychological barriers need to be overcome to achieve weight loss, fitness, and prevent Type 2 diabetes and other lifestyle-related chronic conditions. Health care professionals' attitudes recently have shifted from compliance-seeking and traditional, paternalistic physician-led care to a model in which all are "team members." The individuals who are the subject of the care themselves play an active role, resulting in increased empowerment. In that regard, one of the main factors in preventing and improving outcomes in obesity, diabetes, hypertension, osteoporosis and other chronic conditions is securing the individual's active participation in self-care and care decisions.

Coaching communication and reflection play an important role as well. The most reliable indicator for success is the individuals' internal motivation. This is consistent with studies that have found that the individual's willingness to take responsibility for lifestyle changes was important to success, and enhancing the individual's motivation through coaching was perceived as one of the health care professionals' most important duties.

Contemporary daily activity recommendations for fitness and weight loss are primarily concerned with exercise intensity (100 steps/min speed recommended—3.0 METs), repetition counts (3 or more bouts of at least 1,000 steps each), activity duration (at least 10 min per bout), and basal level of activity (greater than 5,000 steps during the rest of day, totaling 10,000 steps or more). There is nothing inherently "wrong" with these, but by and large, these simple recommendations are rationalized in terms of their amenability to individuals' remembering them and "checking them off" their to-do list each day. Regimens that entail numerous or varied prescribed activities are rightly regarded as too complex or cumbersome for ordinary people to remember or adhere to. However, the simple recommendations are founded on an overly simplistic concept of energy intake and expenditure. Non-exercise activity thermogenesis (NEAT) from standing or other non-sedentary behaviors is neglected. Energy-dissipating neuroendocrine correlates of elevated levels of attention and arousal associated with intermittent walking and postural changes are also ignored by the recommendations.

Furthermore, the standard daily activity recommendations' simplicity is founded on anachronistic notions of people's need to spontaneously remember to do things—in the fashion that prevailed 20 years ago or more. Today, however, nearly every person carries a mobile phone, often containing sensors and sufficient computational power to implement electronic music libraries, and stock-trading applications, video playback, digital camera, and myriad other sorts of software. Sports watches and other electronic wearable devices today similarly contain prodigious computational power and sensors, far beyond what is required for the nominal use-case for which the devices were originally designed. There are presently more than 1,500 health-related software "apps" available from iTunes and Android markets for mobile devices.

It is therefore practical today to create small, wearable devices that can monitor and intelligently analyze patterns of movement that are detected by sensors in such devices, enabling highly varied, complex, and context-aware personalized guidances, as some embodiments of the invention provide, thereby obviating any need for the user to commit any "regimen" to memory.

Evidence suggests that health authorities' recommended goal of 10,000 steps/day may not be sustainable for some groups, including older adults and those living with chronic diseases. Another concern about using the conventional recommendation of 10,000 steps/day as a universal step goal is that it is probably too low for children, an important target population in the war against obesity. Alternative approaches to pedometer-determined physical activity recommendations that are recently showing promise of health benefit and individual sustainability have been based on incremental improvements relative to baseline values. However, most such alternatives continue to be highly simplistic and focus solely on energy balance.

Predominantly as a result of several decades' changes, many professional and service jobs have become progressively more and more sedentary, many people's non-exercise activity level has dropped to very low levels, such that obesity and other health problems have reached epidemic proportions. Accordingly an aim of embodiments of the present invention is to automatically provide alerts or electronic reminders to ambulate, in a fashion that is (a) responsive to an individual's actual activity patterns and behaviors and (b) compatible with routine activities in the workplace and home, so as to facilitate long-term adherence.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Systems, methods, and computer-readable media are provided for promoting positive activity patterns for users and facilitate long-term adherence to the activity patterns, such as by providing alerts or electronic reminders to ambulate in a fashion that is responsive to an individual's actual activity patterns and behaviors and compatible with routine activities in the workplace and home. In particular, embodiments of the present invention are directed to (1) measuring physical activity patterns during the waking hours of a human, and in some embodiments continuously measuring these activity patterns; (2) automatically ascertaining whether the patterns exhibit sufficient frequency and variability of activity such as confers certain health benefits; and (3) if the patterns do not manifest such features, to adaptively provide sensible reminders at irregular within-day intervals such as are likely to establish healthy patterns of ambulation and other light activity.

For example, in one aspect, embodiments of a method of producing entropically-driven reminders includes receiving user-motion information over a time interval for each of a plurality of time intervals spanning a first time period. For a first time interval from the plurality of time intervals, the method determines a time series based on user-motion information received during the first time interval and also based on user-motion information received during each time interval of the plurality of time intervals, which occurred prior to the first time interval. Embodiments of method further comprise determining an amount of activity variability, such as the entropy, for the first time interval, based on the time series and comparing the amount of activity variability to a target threshold. Embodiments of method further comprise generating a pseudorandom value if the amount of activity variability is less than the target threshold, and based on the generated pseudorandom value, which in some embodiments represents logical true or false, determining to provide a notice. In embodiments, a notice is provided if the pseudorandom value represents logical true, and a not provided if the pseudorandom value represents logical false.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

Embodiments of the invention are directed to methods, computer systems, and computer-readable media for promoting positive activity patterns for users and/or facilitating long-term adherence to the activity patterns, such as by providing alerts or electronic reminders to ambulate in a fashion that is responsive to an individual's actual activity patterns and behaviors and compatible with routine activities in the workplace and home. Compared to existing methodologies whose reminders are not adaptive, are emitted with precise recurring periodicity, and quickly become annoying, embodiments of the present invention with contingent, aperiodic, pattern-triggered health-promoting reminding and decision-support action is sufficiently responsive and adaptive to the evolving active and sedentary behaviors of the user so as to mimic the guidance of a health instructor or personal coach. The efficacy of—and sustained adherence to—entropically-guided activity reminders are consequently very high, and the system and method for producing entropically-driven reminders are therefore valuable for preventing or managing conditions such as obesity, osteoporosis, diabetes, and hypertension.

A further aim of embodiments of the invention include establishing and supporting specific temporal patterns of frequent, aperiodic, high-entropy activity as archaeologists and anthropologists believe characterized primitive "hunter-gatherer" cultures for whose members "modern" chronic diseases like obesity, cardiovascular disease, diabetes and other conditions were substantially absent. As such, entropically-guided physical activity promotion serves as a useful adjunct to—but does not replace—other existing state of the art recommendations, including "10,000 steps" and "30-min bout of moderate-to-strenuous exercise at least 5 times per week." The incremental value of entropically-guided activity reminding is particularly significant for individuals of working age who are employed in highly sedentary occupations, who may experience great difficulty adhering to recommendations provided by the existing state of the art.

Figure 1A:
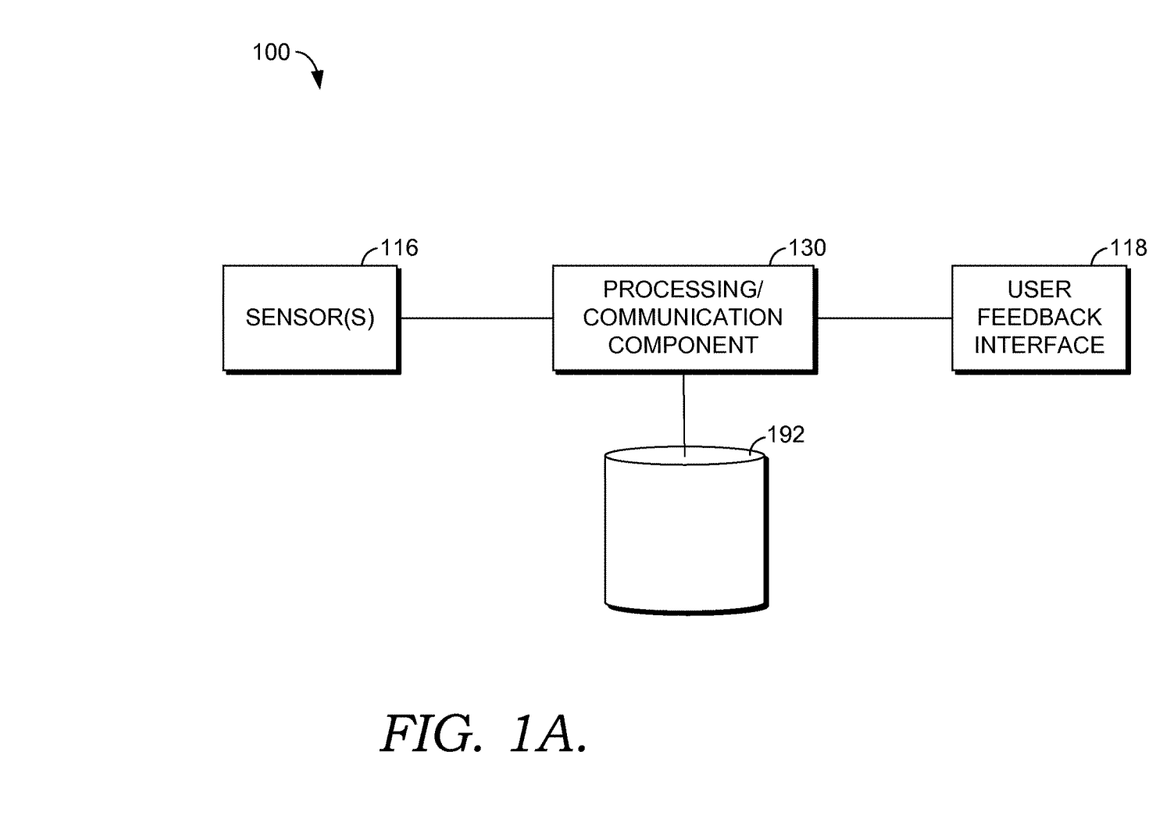
FIG. 1A depicts a block diagram of an illustrative operating environment suitable to implement embodiments of the invention.
Figure 1B:
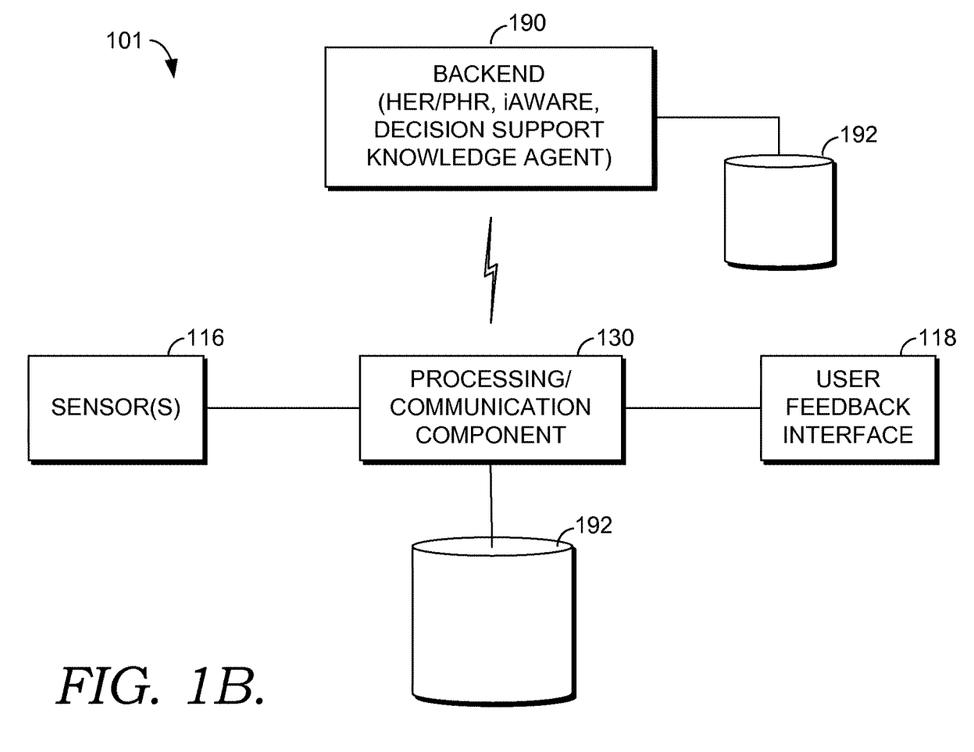
FIG. 1B depicts a block diagram of an illustrative operating environment suitable for practicing an embodiment of the invention.
Figure 1C:
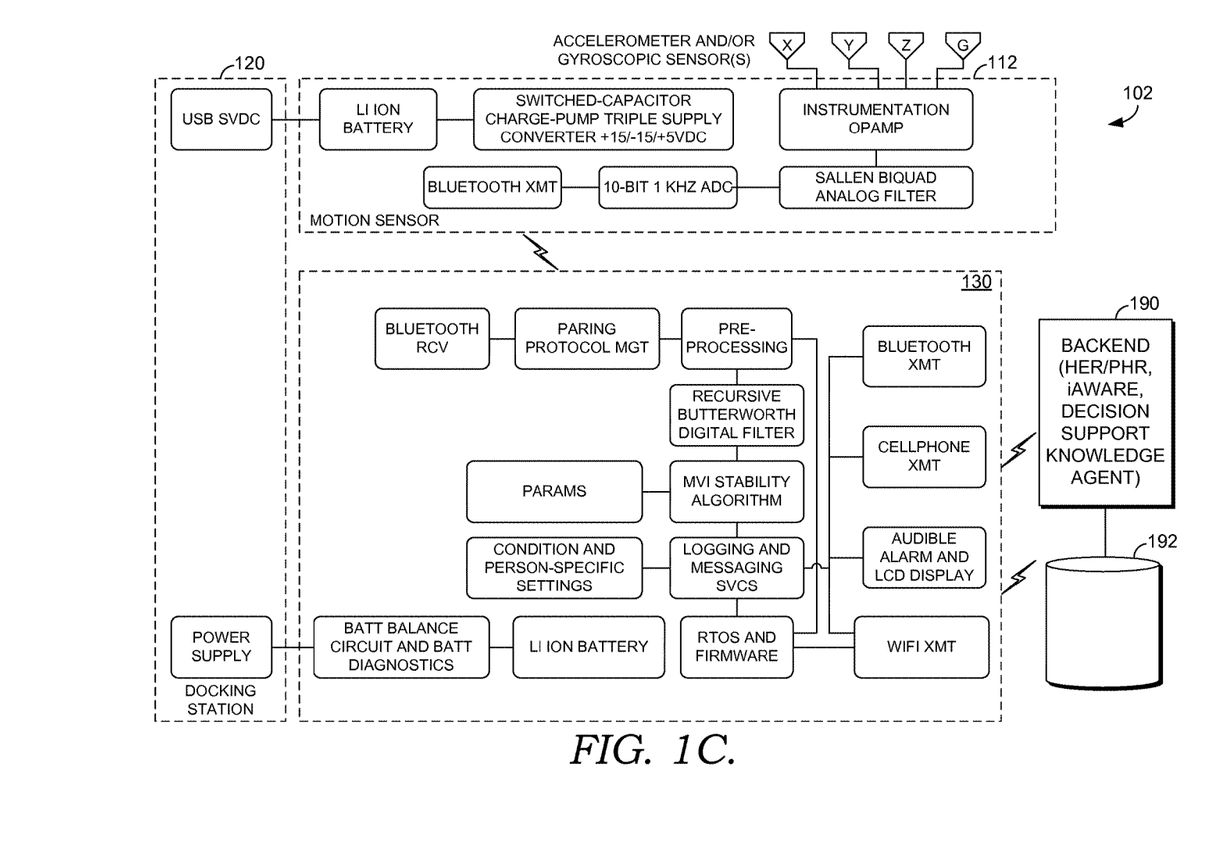
FIG. 1C depicts aspects of an illustrative operating environment suitable for practicing an embodiment of the invention.

Turning now to FIGS. 1A-1C, aspects of illustrative operating environments suitable for use in implementing embodiments of the present invention are provided. FIG. 1A depicts a block diagram of an illustrative example operating environment with which embodiments of the present invention may be implemented designated generally as reference numeral 100. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1A, environment 100 includes one or more sensors 116. In one embodiment, sensors 116 include one or more transducers or types of sensors operable for providing electrical signals corresponding to measurements of various conditions, states, of movements of a user. Embodiments of sensor 116 may further include a power supply, processor, memory operable for acquiring and storing user-information and programming instructions, and communication component for communicating the resulting measurements of user-information with processing/communications component 130. In some embodiments, the transducer may be a standard electrode, such as a single-terminal electrode, or a specialized multi-segment or noise-reduction electrode.

In some embodiments, sensor 116 comprises a stride sensor such as the telemetry Polar S3+® stride sensor, manufactured by Polar Electro Inc. of Lake Success, N.Y., which in some embodiments may be used with in conjunction with a Polar RS800CX® sports watch with a personal-area network (PAN). In some embodiments, sensor 116, processing/communications component 130, and user feedback interface 118 are collocated in a single device which may be worn by the user, while in other embodiments, sensor 116, processing/communications component 130, and user feedback interface 118 may be embodied in separate devices. For example, in one embodiment, sensor 116 is worn on a user's shoe or ankle while processing/communication component 130 and user feedback interface 118 are worn on the wrist like a watch. In another embodiment, component 130 and user feedback interface 118 are embodied on the user's smart phone or mobile device and communicate with sensor 116, which is worn by the user. In such embodiments, sensor 116 may communicate with component 130 via a wireless communication protocol, such as those of existing so called "personal area network" technologies employed by exercise and fitness equipment manufacturers, for example Polar Electro, Nike, and others.

In an embodiment, sensor 116 may be optimally positioned on the user to measure motion. In an embodiment, the accelerometer and gyroscopic chip-sets built into many smart phones may be used as sensor 116. In such an embodiment, the smart phone, running a program for determining user ambulation may monitor user motion, and provide entropically-driven reminders via a user feedback interface, such as user feedback interface 118, described below. Accordingly, in one embodiment, the components of FIG. 1B are embodied on a smart phone or smart watch, which provides functionality for sensor 116, processing/communications component 130, user feedback interface 118, and storage 192.

In some embodiments, multiple sensors 116 may be employed on or about the user. One or more sensors may become compromised, and having multiple sensors provides for robustness. For example a watch sensor may get wet when the user washes his hands and fail to operate as normal, while a second sensor located on the user's ankle or within the user's smart phone may remain effective. In some embodiments, multiple sensors at different locations on the user's body may be employed to obtain more accurate or thorough kinetic information. In such embodiments, motion-signals corresponding to motion in a particular direction or motion may be averaged, or may be weighted or scaled according to the location of the sensor. For example, motion signals obtained from a sensor located on the user's wrist may be weighted less than motion signals obtained from a sensor worn on the user's chest.

In some embodiments sensor 116 includes one or more accelerometeric or gyroscopic transducers operable to determine gyroscopic and/or accelerometer measurement of angular velocity in at least one of 3 axes (pitch, roll, yaw) and acceleration in at least one of 3 axes (X,Y,Z) and to provide motion signals corresponding to this angular velocity or acceleration. For example, in some embodiments, sensor 116 includes one or more transducers, which can take the form of standard MEMS accelerometer integrated circuit chips, for obtaining electrical kinematic signals from the individual. In one embodiment, a plurality of accelerometer sensors and at least one gyroscope sensor, such as the one manufactured by InvenSense Inc that is used in the Nintendo Wii™ Motion Plus® device, may be deployed on a wearable fabric elastomeric band positioned around the chest. Such an embodiment may be used to eliminate or reduce noise, interference, distortion, or artifacts and improve ease-of-use and patient compliance.

In some embodiments, a processor of sensor 116 is operable to control the measurements; for example, to read a transducer's output at certain intervals such as 50 times each second; to pre-process or condition the signal, including applying a threshold, noise-filter, or normalizing the raw user-derived signal; read from or store the user-information in memory, and communicate the acquired time series of user-information with processing/communication component 130. In one embodiment, a floor-threshold is applied such that only movements of a certain magnitude are acquired and communicated to component 130. For example, it may be desirable in some embodiments not to capture every minuscule motion of the user.

Continuing with FIG. 1A, environment 100 includes processing/communication component 130. Exemplary embodiments of component 130 include one or more processors operable for processing sensor information, such as ambulation measures, and for determining variability of activity during time intervals and conditionally and intermittently providing user feedback. Some embodiments of component 130 also include a communication module for receiving information from sensor(s) 116 and, in some embodiments, for communicating results to the user, healthcare provider, back-end decision-support services or other services, and a memory (illustratively shown as data store 192, and described below) as for storing received user-information, determined results, and programming instructions. Component 130 may worn on the user's body, such as clipped to a belt, in a holster, on the user's wrist, or around the user's neck, or can be carried by the user, such as in the user's pocket or purse, or may be kept with a close enough proximity to the user as to communicate with sensor(s) 116. In some embodiments, sensor(s) 116 are housed within or on component 130, as described above.

In some embodiments, component 130 is a smart watch such as the Polar RS800CX® sports watch, manufactured by Polar Electro Inc. of Lake Success, N.Y. In some embodiments, component 130 is a smart phone running one or more application programs or "apps" for receiving user-sensor information of ambulatory measures or other physical activity, determining the degree of variability of activity during ultradian time intervals, conditionally and intermittently providing user feedback, and in some embodiments (such as an embodiment operating in the example operating environment depicted in FIG. 1B) communicating results to the user, health care provider or back-end service. In a smart-phone embodiment, component 130 may use the phone's data communication functionality for communicating user information to a backend, such as a health care provider or decision-support knowledge agent, or a backend service such as a software service for recording and sharing user progress. Advantages of a smart phone embodiment include that it can be more easily be periodically synchronized with data storage, software applications, and other services, which may be present on a user's personal computer, a web-based host service, or other computational services. Additionally, a smart phone embodiment can more easily receive software updates or "app" updates as they become available. In some embodiments, component 130 may use other communication features of the smart phone such as Bluetooth, Wi-Fi, or other personal-area-network—based protocols to communicate with one or more sensors 116 and in some embodiments, a base station or user computer. In certain embodiments, without a smart phone, processing/communications component 130 may nevertheless include functionality for communicating with backend services including periodically synchronized with data storage, software applications, and other services, and receiving software updates.

In embodiments, processing/communications component 130 supports software services (not shown) including one or more software programs or "apps" executed by the one or more processors of component 130. Embodiments of the software services facilitate receiving user-sensor information of ambulatory measures or other physical activity, determining the degree of variability of activity during ultradian time intervals, and conditionally and intermittently providing user feedback. For example, such software services facilitate implementing the method described in connection to FIG. 2, below.

In some embodiments software services also facilitate logging results including information about the frequency and types of reminders provided, user compliance, the amount of physical activity performed by the user, and communicating results to the user, health care provider or back-end service. Some embodiments of software services perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including the 'entropy' package to calculate entropy of accelerometer information acquired from sensor(s) 116, such as one example embodiment "steps-per-15-min" time series acquired from a Polar RS800CX® sports watch personal-area network (PAN) equipped with a telemetry Polar 53+® stride sensor. In some embodiments, software services also include the Apache Hadoop and Hbase framework, or similar frameworks operable for providing a distributed file system, while in some embodiments a suitable operating system is employed.

A smart phone embodying component 130 may be communicatively-coupled with an additional component for facilitating communication with one or more sensors 116, for processing user-information, or for storing and communicating user results. For example, in one embodiment, component 130 is communicatively-coupled to a holster or other component containing a communication module for communicating with one or more sensors 116. Such an embodiment is useful where sensors 116 use a communication protocol that is not compatible with component 130. For example, where sensors communicate using Bluetooth, but component 130 is embodied on non-Bluetooth enabled smart phone, the user may attach a Bluetooth module to the smart phone to enable it to communicate with sensors 116. Similarly, where sensors 116 communicate using Zigbee or another low-rate wireless personal area network platform, a user may couple a Zigbee-enabled communication module to their smart phone. In another example embodiment, a smart phone may be communicatively-coupled with a base station (not shown) located nearby. In one embodiment, the base station could be a personal computer connected to a wireless router or a laptop equipped with RF communication capability such as Wi-Fi or Bluetooth. In one embodiment, the base station communicates with backend services or backend 190 (shown in FIGS. 1B and 1C).

In some embodiments, one or more sensors 116 communicate with other sensors 116 and with component 130 over a wired or wireless communication protocol. In one embodiment, sensor(s) 116 communicate using Bluetooth, Wi-Fi, Zigbee, or similar protocols. In some embodiments a low-powered communication protocol is desirable in order to preserve the batter life of the sensor 116. In some embodiments using a communication protocol having a narrow bandwidth, such as Zigbee, sensors 116 may also include a memory buffer for storing user-derived information until it is communicated to component 130. Sensors 116 may also communicate with other sensors 116 or directly with a base station (not shown), in some embodiments.

In one embodiment, component 130 is a computer system comprising the following hardware and firmware components: a 32-bit 48 MHz AT91SAM7S256 (ARM7TDMI) main microprocessor with 256 KB flash memory and 64 KB RAM, an 8-bit 4 MHz ATmega48 microcontroller with 4 KB flash memory and 512 Bytes RAM, a 26 MHz CSR BlueCore 4 Bluetooth controller with 1 MB flash memory and 47 KB RAM, and 100×64 pixel LCD matrix display. In one embodiment, the generation of reminders at at pseudorandom intervals for providing feedback via user feedback interface 118 (such as haptic reminders and other notices described below in connection to user feedback interface 188) may be performed using a 54C595 8-bit shift register (1-tap, 7-bit LFSR), a 54C86 XOR gate, and two NE555 timer chips, wherein the pseudorandom intervals range from approximately 18 min to 126 min, for example. It should be understood that variations in hardware and firmware are contemplated by and within the scope of the invention, and are provide here for illustrative purposes.

Environment 100 of FIG. 1A also includes user feedback interface 118. Embodiments of 118 facilitate providing information to the user such as the entropically-driven reminders, other feedback regarding the users physical activity, or information related to the users physical activity or operation of the device or components of the device. For example, in one embodiment such information might include a report indicating an amount of physical activity performed by the user over a time interval, a target amount of physical activity that the user desires to achieve, and/or a comparison of the amount of activity the user has performed vs. the target amount. In one embodiment, this information might include compliance information indicating the number and frequency of the entropically-driven reminders provided to the user and whether the user responded to the reminders by increasing physical activity, for example. In one embodiment, this information might include an indication that sensor(s) 116 are detected and communicatively coupled to component 130, for example.

Embodiments of user feedback interface 118 may comprise one or more of a speaker, alarm, or sound producing component, for generating an alarm, or other audible feedback; a vibrating component for providing haptic (tactile vibration) feedback; a display component for displaying messages, alerts, notices, or other visual feedback to the user, or similar interfaces for providing information to a user. In some embodiments, interface 118 is part of a smart phone or smart watch and uses components of the smart phone or watch to provide feedback information to the user. For example, the display screen, the speaker, and/or the vibrating component of the phone may be used as interface 118 in one embodiment. In some embodiments, feedback may be provided in the form of an SMS text message or email, which may be displayed or accessed using the phone.

In some embodiments, the user feedback may be communicated to backed services, such as logging or tracking software, or sent to a health care provider or another family member. In some embodiments, such as embodiments where various types of feedback-reminders are provided to the user (e.g., alarm, text message, playing back a voice recording, vibrating, or similar feedback), component 130 or component 130 in conjunction with services operating on backend 190 (described below in connection to FIG. 1B), monitor the effectiveness of the feedback provided. For example, in some embodiments the type and frequency of reminders or other feedback is logged as well as subsequent level of physical activity performed by the user so that the effectiveness of types and timings of reminders for that particular user can be determined. Software services, such as decision-support knowledge agent software operating on backend 190, may then analyze the user patterns and respond accordingly, such as by adapting the types and frequency of responses provided by the user, modifying the user's targeted activity level, or preparing the information for reporting to a health care provider or insurance provider. In so doing these embodiments can learn to be more responsive to the user.

Turning briefly to FIG. 1B, an illustrative operating environment 101 is shown that includes the components of environment 100 of FIG. 1A, but also includes backend 190. In some embodiments, component 130 communicates directly with backend 190. Embodiments of backend 190 can include health care provider computer systems and services, case-management software, electronic health record decision-support systems and services, and consumer personal health record systems and services, for example. In some embodiments, backend 190 includes software functionality enabling it to perform as a server, while component 130 includes software functionality enabling it to perform as the client.

Referring now to FIGS. 1A and 1B, in some embodiments, component 130 stores information on data store 192, which may be local or remotely located, and which may be accessible by backend 190, in some embodiments. In some embodiments, data store 192 comprises networked storage or distributed storage including storage on servers located in the cloud. Thus, it is contemplated that for some embodiments, the information stored in data store 192 is not stored in the same physical location. For example, in one embodiment, one part of data store 110 includes one or more USB thumb drives or similar portable data storage media. Additionally, information stored in data store 192 can be searched, queried, analyzed via services operating on backend 190, such as by a health care provider or by a decision-support knowledge agent, for example.

Turning now to FIG. 1C, aspects of an illustrative operating environment suitable for practicing an embodiment of the present invention are provided and referred to generally as environment 102. As shown in FIG. 1C, an embodiment of processing/communication component 130 is communicatively coupled to wearable motion sensor 112, which is one embodiment of sensor 116, and docking station 120. In the embodiment shown in FIG. 1C, docking station 120 recharges a battery in component 130 and in sensor 112. In some embodiments, docking station 120 may comprise 2 docking or recharging stations: one for component 130 and one for sensor 112. Component 130 is communicatively coupled to backend 190, and data store 192, which are described previously in connection to FIGS. 1A and 1B.

In environment 102 of FIG. 1C, motion sensor 112 includes one or more accelerometers or gyroscopic transducers. In this embodiment, the transducers are coupled to an instrumentation operational amplifier, an analog filter, an analog-to-digital converter, and a Bluetooth or similar RF communication component, thereby enabling motion sensor 112, when positioned on the user, to obtain raw motion signals of the user, capture and digitize the raw motion signals, and communicate this information to component 130. Motion sensor 112 also includes a power supply made up of a battery and multiple-output supply converter.

In the embodiment shown in FIG. 1B, component 130 includes a Bluetooth or similar RF communication component operable to receive user-information from motion sensor 112 or from other sensors 116, preprocessing and filtering components operable to condition and format the received user information for determining the degree of variability of activity during ultradian time intervals and conditionally and intermittently providing user feedback as described in connection to FIG. 2, below, and in some embodiments communicating results to the user, health care provider or back-end service. Embodiments of component 130 shown in FIG. 1C may also include a Bluetooth, cell-phone, or Wi-Fi communication component for communicating information to backend 190, data store 192, and/or user feedback interface 118 (not shown), which may be embodied within the same device as component 130, such as in the form of an alarm or display for providing entropically-driven reminders, diagnostic feedback, power levels, and other information to a user or for receiving inputs from a user such as parameters and device settings, as described above in connection to FIG. 1A. Embodiments of component 130 may also include memory for storing parameters, settings, firmware and programming instructions, and determined results. Embodiments of component 130 may also include a power supply which in one embodiment comprises a battery and a battery balance circuit. In one embodiment, component 130 is a computer system with one or more processors, memory, and input/output functionality.

Figure 2:
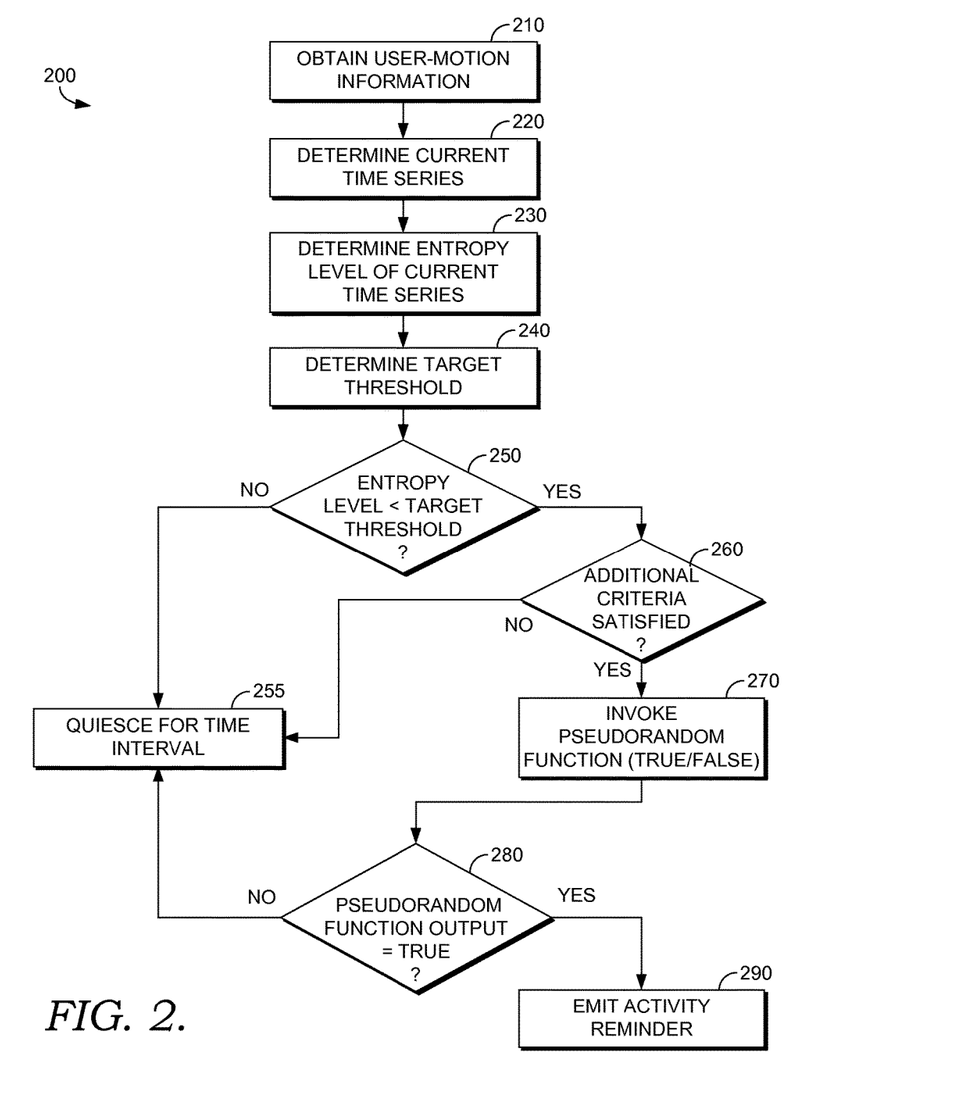
FIG. 2 depicts a flow diagram of a method for promoting positive activity patterns for users and facilitating long-term adherence to the activity patterns, by providing entropically-driven activity reminders, in accordance with an embodiment of the invention.

Turning now to FIG. 2, a flow diagram is provided illustrating an exemplary method 200 according to one embodiment. At a high level, a flow diagram illustratively depicts a method 200 for promoting positive activity patterns for users and facilitate long-term adherence to the activity patterns, by providing entropically-driven activity reminders to ambulate in a fashion that is responsive to a user's actual activity patterns and behaviors and compatible with routine activities in the workplace and home. In embodiments, the steps of method 200 are carried out for a time period $\tau$, wherein $\tau$ represents an ultradian time interval, in some embodiments. In particular, in some embodiments $\tau$ is less than 90 minutes, and preferably is between 10 and 30 minutes, although other time intervals may be used.

In contrast to known methodologies for encouraging individuals to adopt healthy activity patterns, embodiments of present invention do not focus as much on energy balance but instead aim to establish patterns of frequent ambulation at irregular time intervals resembling high-entropy patterns that characterize a subsistence "Hunter-Gatherer" life-style. With continuing reference to FIG. 2, in some embodiments, the entropy of a time series signal (such as "steps-per-15-min" or other time series captured from MEMS accelerometer chips or other sensor(s) 116, such as are routinely part of smart phones, sports watches, and other wearable mobile devices) is continuously calculated and used to trigger personalized, context-adaptive electronic reminders for users wearing or holding devices. Narrow statistical distributions of step counts have low entropy (contain little information); wide Hunter-Gatherer-type distributions have high entropy (contain more information) and are associated with beneficial changes in endocrine systems and dynamic gene-expression regulation.

It has been proposed that relatively low intensity exercise induces moderate growth hormone (Gil) responses through activation of the central cholinergic system, resulting in a reduction in hypothalamic somatostatin release. However, it appears that there is an upper limit to this process and at higher exercise intensities, once hypothalamic somatostatinergic tone is completely suppressed, further increases in GH release must be mediated by an increase in growth hormone releasing hormone (GHRH) secretion. The inhibition of somatostatinergic tone as a result of brief bouts of exercise is accompanied by suppression of the GH response to treadmill exercise, at 60% VO2max, following pretreatment with the somatostatin analogue octreocide, in humans. In contrast, administration of the somatostatin inhibitor, pyridostigmine, enhances activity-induced GH release, suggesting that pyridostigmine and exercise might act independently in eliciting the GH response to exercise. Besides GH and GHRH effects, physical activity induces significant increases of IL-6, cortisol, and leukocytes in comparison to the low-intensity protocols. Non-exercise physical activity thennogenesis (NEAT) is also important in net daily energy balance and neuroendocrine function.

Lifestyle-related diseases are rapidly increasing at least in part due to less physical activity. Duration, intensity, and frequency have been utilized by current state of the art methodologies to guide health recommendations, but not measures of the ultradian variability of activity. Context-sensitive electronic reminders to ambulate (low-dose non-exercise activity) frequently and at varied, irregular intervals during each day constitute a "minimum movement entropy dose" as part of a comprehensive exercise prescription. Exceeding a minimum entropy threshold is necessary, but is not by itself sufficient for health. The conventional "calorie intake not exceeding the calories expended" energy balance exercise prescriptions continue to be valid and valuable. However, energy balance-based exercise prescriptions may not be effective. Even if overtraining or other complications do not arise, a daily regimen of vigorous exercise may reach a point of diminishing returns. Activity-induced change in body weight obscures the large inter-individual variability in body weight and compensatory responses. Compensatory changes in appetite and metabolism tend to neutralize the beneficial effects of structured exercise regimens. Individuals who experience a plateau or lower-than-predicted weight loss tend to experience strong compensatory physiologic and behavioral changes that effectively offset the net increase in energy expenditure.

The effect of increased unstructured activity need not be weight loss necessarily but increased health and fitness at a stable weight, as has been emphasized recently by the Health At Every Size (HAES) movement. Instead, a more highly-varied (higher entropy) pattern of frequent ambulation and other light activity may be sufficient to promote health goals including fitness, weight loss, maintain non-increasing weight. Within broad limits, the higher the entropy of the activity time series, the better (with regard to weight loss and other health goals). Entropy values greater than 2.1 are preferred. Values less than 1.2 suggest insufficient variability to induce the alterations in gene expression and other adaptations in muscle and other tissues that are associated with improvements in metabolism.

The health beneficial effects of regular physical activity include metabolic adaptations in skeletal muscle, which are thought to be elicited by cumulative effects of transient gene responses to each bout of exercise, but how is this regulated? A potential candidate in this is the transcriptional co-activator peroxisome proliferator-activated receptor-gamma co-activator (PGC)-Ialpha, which has been identified as a master regulator of mitochondrial biogenesis, but also been shown to regulate proteins involved in angiogenesis and the anti-oxidant defense as well as to affect expression of inflammatory markers. Exercise increases PGC-Ialpha transcription and potentially PGC-Ialpha activity through post-translational modifications, and concomitant PGC-Ialpha-mediated gene regulation is suggested to be an underlying mechanism for adaptations in skeletal muscle, when exercise is repeated. The current review presents some of the key findings in PGC-Ialpha-mediated regulation of metabolically related, anti-oxidant and inflammatory proteins in skeletal muscle in the basal state and in response to exercise training, and describes functional significance of PGC1 alpha-mediated effects in skeletal muscle. In addition, regulation of PGC-Ialpha expression and activity in skeletal muscle is described. The impact of changes in PGC-Ialpha expression in mouse skeletal muscle and the ability of PGC-Ialpha to regulate multiple pathways and functions underline the potential importance of PGC-Ialpha in skeletal muscle adaptations in humans. The absence of exercise-induced PGC-Ialpha-mediated gene regulation during a physical inactive lifestyle is suggested to lead to reduced oxidative capacity of skeletal muscle and concomitant impaired metabolism. PGC-Ialpha overexpression caused hepatic insulin resistance, manifested by higher glucose production and diminished insulin suppression of gluconeogenesis. Paradoxically, PGC-Ialpha overexpression improves muscle insulin sensitivity, as evidenced by elevated insulin-stimulated Akt phosphorylation and peripheral glucose disposal. PGC-Iinsufficiency may predispose toward PAD or exacerbate its severity or rate of progression or both.

Even though most of these pathways are activated by different stimuli and in a temporally and spatially separated manner during exercise, many of the major signal transduction events converge on the peroxisome proliferator-activated receptor γ co-activator 1α (PGC-1α) by post-translationally modifying the PGC-1α protein, modulating PGC-1α gene expression or both. In turn, depending on the cellular context, PGC-1α regulates specific gene programs. Ultimately, PGC-1α modulates most of the transcriptional adaptations of skeletal muscle to exercise. Emerging evidence suggests that normal physiological adaptations to a heavy lipid load depend on the coordinated actions of broad transcriptional regulators such as the peroxisome proliferator activated receptors (PPARs) and PPAR gamma co-activator 1 alpha (PGC1 alpha). The application of transcriptomics and targeted metabolic profiling tools based on mass spectrometry has led to our finding that lipid-induced insulin resistance is a condition in which up-regulation of PPAR-targeted genes and high rates of beta-oxidation are not supported by a commensurate up-regulation of tricarboxylic acid (TCA) cycle activity. In contrast, exercise training enhances mitochondrial performance, favoring tighter coupling between beta-oxidation and the TCA cycle, and concomitantly restores insulin sensitivity in animals fed a chronic high-fat diet. The exercise-activated transcriptional co-activator, PGC1 alpha, plays a key role in coordinating metabolic flux through these two intersecting metabolic pathways, and its suppression by overfeeding may contribute to diet-induced mitochondrial dysfunction. Our emerging model predicts that muscle insulin resistance arises from a mitochondrial disconnect between beta-oxidation and TCA cycle activity. Understanding of this "disconnect" and its molecular basis may lead to new therapeutic approaches to preventing and managing obesity and metabolic diseases such as Type-2 diabetes.

It is known that transcription of the PGC-1α gene can be either inhibited or stimulated by p38 MAP kinase (p38 MAPK). Furthermore, basal Akt-dependent signaling is affected by PGC-1α expression levels. The p38 MAPK-induced PGC-1α gene transcription is prevented by insulin. Insulin suppression of PGC-1α gene transcription is in turn neutralized by overexpression of the FoxO1 gene. Essentially, transcription of the PGC-1α gene is balanced by different intracellular signaling pathways, which affect a diverse metabolic and vascular physiologic pathways.

Endurance exercise is known to induce metabolic adaptations in skeletal muscle via activation of the transcriptional co-activator peroxisome proliferator-activated receptor γ co-activator 1α (PGC-1α). PGC-1α regulates mitochondrial biogenesis via regulating transcription of nuclear-encoded mitochondrial genes. In response to acute altered energy demands, PGC-1α re-localizes into nuclear and mitochondrial compartments where it functions as a transcriptional co-activator for both nuclear and mitochondrial DNA transcription factors. These results suggest that PGC-1α may dynamically facilitate nuclear-mitochondrial DNA crosstalk to promote net mitochondrial biogenesis, which in turn affects the rate at which the body metabolizes nutrients and utilizes energy.

PGC-1α is a transcriptional co-activator that powerfully regulates many pathways linked to energy homeostasis. Specifically, PGC-1α controls mitochondrial biogenesis in most tissues but also initiates important tissue-specific functions, including fiber type switching in skeletal muscle and gluconeogenesis and fatty acid oxidation in the liver. S6 kinase, activated in the liver upon feeding, can phosphorylate PGC-1α directly on two sites within its arginine/serine-rich (RS) domain. This phosphorylation significantly attenuates the ability of PGC-1α to turn on genes of gluconeogenesis in hepatocytes, while leaving the functions of PGC-1α as an activator of mitochondrial and fatty acid oxidation genes completely intact. These phosphorylations interfere with the ability of PGC-1α to bind to HNF4a, a transcription factor required for gluconeogenesis, while leaving undisturbed the interactions of PGC-la with ERRa and PPARa, factors important for mitochondrial biogenesis and fatty acid oxidation. Experimental data reveal that S6 kinase can modify PGC-1α, providing metabolic flexibility needed for dietary adaptation.

The network of inter-related up- and down-regulation of PGC-1α—and other genes involved in energy/metabolism pathways and mitochondrial biogenesis and capacity for insulin sensitivity and glucose and fatty-acid oxidation such as AMPK, p38 MAPK, CaMKII, Akt/PKB, mTOR, S6K, p70S6k, 4E-BP1, MKK3 and MKK6, CREB, ATF-2, HDAC4, MEF2, STARS, adiponectin, SIRT3, TNF-alpha, and HIF-2alpha—occurs on an ultradian timescale (5 min to 180 min). Several hours after completing a bout of exercise, the concentrations of gene products and gene expression levels have reverted to baseline levels. This possibly explains why 30 min of moderate to vigorous exercise once per day may not achieve the intended effect in terms of weight loss, diabetes prevention, or other goals. Instead, a more highly varied pattern of intermittent light activity occurring at irregular intervals throughout the day may result in gene-expression and other physiologic adaptations that more consistently improve metabolism and fitness, despite a comparatively small average daily exercise dose.

The current state of the art for activity reminding and exercise prescribing has several limitations, including:

(1) The measurement and analytics methods address only circadian or weekly or other longer timescale patterns, and do not address ultradian (short timescale) patterns' relationship to fitness, which may provide numerous advantages, as indicated in the discussion of the preceding paragraphs.

(2) The underlying principles are solely based on energy intake/expenditure balance, and do not take into account activity-induced up- and down-regulation of the expression of certain metabolism-related genes such as PGC-1α that are related to muscle and organ system metabolism, cardiovascular function, and functioning of endocrine organs and receptors.

(3) The reminders or recommendations are emitted at precise, scheduled intervals, often without adequate (or any) personalization or reflection of recent user actions and behavior. Standardized, routinized messages are overly regimented or intrusive. After a short period of use the reminders become perceived as "nagging" or "boring", such that most users soon opt to ignore the advice or cease using the device and software application.

(4) Existing static, overly-simplistic models lack an adequate abstraction of user psychology, and the motivations for accepting and adhering to, vs. rejecting, coaching recommendations.

Accordingly, it is therefore highly valuable and highly desirable to provide embodiments of the methods and systems described herein, for mitigating the aforementioned limitations, particularly embodiments of the invention that are also not susceptible to biases, that are tolerant of modest amounts of missing or sensing-artifact contaminated values of model-variables information, that take advantage of longitudinal trends and physiological causation of trends, and that do not require extensive or intrusive questioning or detailed self-reported information from patients. Moreover, excellent adherence to physical activity prescriptions is essential for the successful prevention or management of obesity, hypertension, osteoporosis loss of bone mineral density, sarcopenia (weakness and muscle loss), and falls risk.

Continuing with reference to FIG. 2, several presently available health promotion wearable monitors (such as Jawbone's UP® wrist band device) include an option to request periodic activity reminders, usually by an inaudible vibration signal that is sensible on the skin near the wearable monitoring device. But as previously described, if such activity reminders are periodic (intensive reminders, always emitted at the same interval) then a user is likely to fall into a pattern of noncompliance. Over time, the repeated reminding at a fixed rate is ignored at a progressively higher percentage of the time. The monitoring device is viewed as a "nag" and one that can be ignored with impunity, so that the reminding is ineffective in longterm chronic use.

If, on the other hand, activity reminders are (a) varied and interesting, emitted at irregular intervals, and (b) situationally/contextually sensitive, emitted only at times when the historical pattern of activity indicates that the user has been excessively sedentary (as is true of the present invention), then adherence/compliance is sustained indefinitely in a higher percentage of people, and there is a greater probability of achieving the user's health goals.

With particular reference to activity reminders that are situationally/contextually sensitive, in one exemplary embodiment of the invention, a prototype was implemented with a linear feedback shift register (LFSR) pseudo-random interval generator being conditionally triggered by entropy values that were below a target threshold. In operation, the entropy-triggered LFSR emitted only about 36% as many reminders per day, compared to another embodiment (an early prototype version) that utilized always-on LFSR random triggering. It is possible that compliance with a high-entropy, hunter-gatherer-type pattern of activity is enhanced in part due to the user's learned behaviors that involve more frequent spontaneous initiation of ambulation at irregular intervals, which has the consequence of avoiding low-entropy triggering of reminders. In this way, the user's adoption of a behavioral change that entails moderate spontaneous movement with spectral peaks covering a wide range of frequencies is rewarded by the total cessation of reminders. Embodiments of the monitoring device then are viewed as a "coach"—an intelligent and fair agent whose decisions exhibit attentiveness and factual insight into the user's own actions—and not as a "nag". Accordingly, the artificial intelligence exhibited by these embodiments emulates a sort of social support, characterized by haptic 'presence' that is predominantly affirmative: silent when spontaneous behaviors are conforming to goals and reinforcing incremental improvements, and only intervening or intruding when a necessary corrective action is factually indicated.

Additionally, implementation of the prototype has shown that the duration of the activity reminder (such as a haptic tactile vibration alert on a wrist band, or other embodiments of user feedback interface 118, as described above in connection to FIGS. 1A and 1B) was strongly correlated with compliance rate. Reminders that lasted less than 10 seconds were complied with only 24% of the time, while reminders of 30 sec duration or more were associated with 91% compliance.

Health researchers have found that psychologically well-suited social support and reminders are related to positive health outcomes across a broad range of disease contexts, for example diabetes and heart disease. Reminding patterns can include (1) regular reminding that was habitually offered, (2) situational reminding adapted to changing circumstances or behaviors, and (3) intensive reminding, either regular (i.e., nagging) or situationally varied. Instrumental helping involves monitoring activity and measuring whether behavior is trending in favorable or unfavorable directions. Coaching involves context-adaptive reminding, shaping behavior by reinforcing incremental gains and offering a variety of affirmation messages (e.g., "It has been more than 72 hours since I had to remind you to get up and walk around. Great work!" or shorter "SMS language" or yet shorter symbolic emoticons).

Social support researchers have wrestled with a contradiction that research in this area has produced, namely, perceived social support correlates with a range of positive physical and psychological outcomes, but received social support very often is associated with negative impacts on well-being. Some researchers have explored ways to resolve this contradiction. They suggest that being the recipient of social support in times of stress could lower self-esteem because it highlights the support recipient's inability to manage the situation without help. One proposal is that some effective support might be "invisible," that is, the support provider could describe the actual support given, but the support recipient would not have perceived it. In embodiments of the present invention, monitoring the user's ambulation has an "invisible" component in that if the user had spontaneously ambulated, the supportive partner did not need to point it out to the partner. Coaching also had an "invisible" aspect to it in that it came in the form of suggestions, interactive exchange, and/or congratulations/affirmations. Also, regular reminding had become an ingrained habit and as with most habits, is after a time not particularly noticed. Effective reminding requires dynamic adaptation and responsiveness to actual behavior.

Still with reference to FIG. 2, as described above, in some embodiments, the steps of method 200 are carried out for a time period τ, which may represent ultradian time interval. At a step 210, user-motion information is obtained. In embodiments, user motion information is received from sensor(s) 116 and may comprise measured ambulation or other physical activity measured by sensor(s) 116. In one embodiment, step 210 includes measuring and recording ambulation from signals provided by a wearable accelerometer sensor 116 in the form of user steps (or units of movement). The steps (or units of movement) are detected, counted and summed in memory.

At a step 220, a time series is determined for the current time period τ. In embodiments, the information obtained in step 210 (for example, the counted and summed steps (or units of motion) for the current time period) are deposited into a time series. The time series may be implemented in any number of was as are known in the art. In some embodiments, the time series includes summed steps for only a limited number of recent time intervals, such as for example time intervals over the previous 24 hour period, the previous 3 days, week, or other time span. In some embodiments, all step- or unit-motion-count information is stored in a record so that it can be accessed at a later time.

In one embodiment, the time series is implemented using a circular buffer 1-dimensional array. In one embodiment, the array contains 1440/τ bins, wherein each bin's value is the total number of steps (or units of motion) counted in a τ-min time interval. (In this embodiment, 1440 represents the number of minutes in a 24 hour period.) In one embodiment, τ is preferably between 10 and 30 minutes. In some embodiments using the circular buffer, to enable step-counts for a current τ interval that is commencing to be accumulated, the cell at the tail-end of the buffer may be zeroed out or cleared, and all values in the buffer shifted leftward one position, thereby updating the buffer. Or alternatively, in those embodiments, the pointer to the head of the circular buffer may me incremented by one so that it now points to another bin (which becomes the new head) of the buffer. The time series for the current period is then determined by storing the counted steps (or units of motion) for the current time period into the bin indicated by the pointer (i.e. the current head of the buffer).

At a step 230, a quantitative measure of variability based on the current time series is determined. In embodiments the measure of variability comprises a Shannon, Jeffreys, Laplace, Minimax, Tsallis, Chao-Shen, Dirichlet, Miller-Madow, James-Stein Shrinker, or Nemenman-Shafee-Bialek (NSB) entropy, or other measures of variability such as RMSSD or other measures such as are known to those practiced in the art. In one embodiment for the quantitative measure of variability determination, the entropy may be expressed as:

$$H = -\sum_{i=1}^{N} (p(a_i) * \log(p(a_i)))$$

In some embodiments, as the entropy level (or other quantitative measure of variability) is determined for each time interval τ, that determined entropy level is stored in data store 192 such that it and the entropy levels determined for previous time intervals are accessible by component 130, so that analysis may be performed based on, for example, comparing most recently determined entropy level with the entropy level of the previous time interval, or entropy level of a particular past time interval. In embodiments, the entropy level determined for current time series may be referred to as the "current entropy" (or "current entropy level"); the entropy level determined for the previous time interval referred to as the "previous entropy." Accordingly, in embodiments, with each new time interval and determination of entropy level corresponding to that time interval, the value of the "current entropy level" will become the value of the "previous entropy level."

At a step 240, a target threshold is determined. In embodiments, the target threshold corresponds to an amount of physical activity desired to be performed by the user (usually a minimum amount of activity desired, although in some embodiments, such as where a user desires to avoid or minimize physical activity, this threshold could represent a maximum). Thus, embodiments of this step determine the value that corresponds to a desired variability level for comparing (in a step 250) with the quantitative measure of variability determined in step 230. In one embodiment, the target threshold is a value that corresponds to a given amount of physical activity during the time interval, such as minutes of movement or ambulation, units of motion, number steps taken, or similar measure. In some embodiments, this target threshold value is set or provided by the user or health care provider, and in some embodiments, the target threshold is adaptive, for example, it may increment as the user's fitness improves. In some embodiments, the value is based on the amount physical activity recently performed by the user, or typically performed by the user over recent days, weeks, or months. For example, a "training program" feature of software services operating on component 130 may incrementally adjust the threshold in order to motivate the user to continue to increase the level of physical activity performed. In some embodiments, the threshold is provided by the user via a user interface, which in some embodiments may be part of user feedback interface 118. In one embodiment, a software program such as an "app" running on component 130, has a setting wherein a user may specify a desired minimum amount of physical activity (such as number or steps or minutes of ambulation, or other units of motion or physical activity). Similarly, the app may also provide the user with an option to specify the ultradian time interval τ. In one embodiment a health care provider may specify the threshold (or τ, or both) via a software service on backend 190.

At a step 250, a comparison is performed between the current entropy level and a target threshold. In embodiments, a current entropy level which exceeds the threshold suggests that the user has at least performed a minimum desired level of physical activity over the time interval τ. Accordingly, where the entropy level (or other quantitative measure of variability) or measure of physical activity over the time interval exceeds the target threshold, then the method proceeds to step 255 and quiesces until the current time period has elapsed. On the other hand, a current entropy level which does not exceed the threshold is indicative of the user not having performed the minimum desired level of physical activity over the time interval τ. Thus, where the target threshold exceeds the entropy level (or other quantitative measure of variability) or measure of physical activity over the time interval, then the method proceeds to step 260, in some embodiments. In some embodiments, the result of the comparison of step 250 is recorded or logged, so that for example a user or health care provider can look back and determine how many time intervals the desired minimum activity was achieved or not achieved. In some embodiments a counter or log is kept of intervals where the threshold was and/or was not exceeded. Such counter or log may be referenced to determine additional criteria in step 260, in some embodiments. For example, one criterion might be whether the target threshold exceed the previous entropy level, thus in this embodiment, a log of recent comparisons of step 250 might be accessed to determine the outcome of the previous comparison. Additional criteria are described below in connection step 260.

In some embodiments, where the target threshold exceeds the entropy level other measure over the time interval, then the method skips step 260 and proceeds to step 270. It is also contemplated that in some embodiments where the target threshold exceeds the entropy level other measure, the method proceeds directly to step 290 where an activity reminder is emitted.

At step 260, it is determined whether an additional criterion (or criteria) are satisfied in order to potentially emit a reminder to the user. For example, in some embodiments, method 200 only proceeds to step 270 if a second criterion is also satisfied (wherein the first criterion refers to the target threshold exceeding the entropy level). In embodiments, where the one or more criteria are satisfied in step 260, the method proceeds to step 270; but where the one or more criteria are not satisfied, the method proceeds to step 255. Examples of an additional criterion (or criteria) to be satisfied include, for example, that the entropy level determined for the previous time interval (the previous entropy level) was also determined to be below the target threshold. (This implies that the user has failed to achieve a minimum level of ambulation or physical activity for two consecutive time intervals.) In another example criterion, the threshold has exceeded the entropy level for at least a specified number of intervals over the past 24 hours, such as for example at least eighty percent of the intervals. In another example, the criterion is that it has been greater than a certain amount of time, such as 8 hours since a reminder was emitted. In some embodiments, multiple criteria may be evaluated at step 260, such that all criteria may be to be satisfied, or any one of a set of criteria satisfied. For embodiments which include step 260, specific additional criteria utilized should be considered in light of the above discussion regarding effectiveness of the activity reminder so as not to result in overly reminding ("nagging") the user nor to so rarely remind the user (when the user is not performing a desired level of activity) as to be ineffective.

At a step 270, a pseudorandom function is invoked. Embodiments of this step use a pseudorandom function to provide an output that is either logically true of false. In embodiments, a purpose for this step is to provide a degree of randomness regarding whether or not to emit an activity reminder to a user, when conditions are present that warrant the user receiving such a reminder (e.g., the current entropy level is below the target threshold and an additional criteria is satisfied (such as the previous entropy level also being below the target threshold). Thus, even where the user is performing in a manner that "needs" an activity reminder, an activity reminder is not necessarily provided. In embodiments, this results in the activity reminders being emitted at non-regularly occurring times. In one embodiment, a linear feedback shift register (LFSR) and an XOR gate (such as a 54C86 XOR gate) are used to provide a pseudorandom output. For example, in this embodiment, applying steps 250 and 260, if entropy level is below the target threshold and the I interval just completed was the second such below-entropy-threshold interval, then at step 270 enable the clock signal input to the pseudo-random interval generator (i.e. the LFSR and one-tap XOR gate). In one embodiment, the pseudorandom function is provided by a software function.

In some embodiments, the output of the pseudorandom function may be weighted such that, although still random, the output is biased to be logically true or false for a certain percentage of time other than fifty percent. For example in one embodiment, the output is "true" twenty-five percent of the time and the output is "false" seventy-five percent of the time. This embodiment of step 270 may be used in some embodiments where the method 200 does not include step 260. Thus, having a pseudorandom function output true (and therefore result in an emission of a reminder) less than fifty percent of the time, may provide entropically-driven reminders at a frequency not likely to annoy or be dismissed by the user.

At a step 280, based on the outcome of the pseudorandom function of step 270, the method proceeds to step 290 or to step 255. For example, where the pseudorandom output is a first value corresponding to logically true (or "high" or 1), then the method goes to step 290. But where the output is a value corresponding to logically false (or "low" or 0), then the method proceeds to step 255. In one embodiment using the LFSR and XOR gate, if the output of the pseudo-random generator's XOR gate goes to a logical-high "true" value, then proceed to step 290 and emit an activity reminder signal to the human user.

At a step 290, an activity reminder is emitted. Although the term "activity reminder" is used, it is contemplated that any variety of notices or other feedback may be emitted in embodiments at step 290 including, for example, the various types of feedback described above in connection with user-feedback interface 118. For example, in some embodiments, a reminder may take the form of an alarm, music, or voice recording, or other audible feedback, haptic feedback, displaying a message, alert, notice, or other visual feedback provided to the user, an SMS message or email, which may be provided to the user, a health care provider, or another person such as a family member. In some embodiments, the type of reminder emitted may be specified by the user or healthcare provider (for example in a user-preferences feature of software services operating on component 130). In some embodiments, the type of reminder is determined based on the types of previously emitted reminders, and in some embodiments based further on the effectiveness of those reminders. Thus in some embodiments, the types of reminder may be varied or repeated based on the effectiveness of previously emitted types reminders, as determined by component 130 (or component 130 operating in conjunction with services on backend 190) as described above in connection with component 130. For example, in some embodiments, the reminder types are varied. While In some embodiments, previous reminder types that were effective may be used again, and where previous reminder types were ineffective, another type of reminder may be used. In one embodiment, effectiveness of the reminder and reminder type is based on whether the entropy level for the time interval following the emission of the reminder exceeds the target threshold. In another embodiment, effectiveness is based on whether the entropy level for the time interval following the emission of the reminder is greater than the entropy level for the time interval for which the reminder was issued. (In other words, the user increased ambulation or physical activity, even if it was not enough to exceed the target threshold.) In some embodiments, the type of reminder emitted and the time of the reminder is recorded.

At a step 255, the method enters a quiescent state for the remainder of time interval. In this state, no reminders are emitted for the remainder of the time interval either because the user has achieved sufficient ambulation or the outcome of the pseudorandom function (step 270) was false, 0, or a logical low, which results in no reminder being issued, in some embodiments. In some embodiments, after step 255, or 270, the method 200 returns to step 210. In some embodiments, at the end of time interval τ, method 200 returns to step 210. In some embodiments, method 200 is performed for ultridian time intervals throughout a 24 hour period, or throughout a user's waking day.

In some embodiments, a device comprising sensor(s) 116, component 130 executing computer instructions embodying method 200, and user feedback interface 118, acquires baseline "steps-per-15-min" counts time series during the user's initial use of the device. During the initial period while much of the system's time series memory contains zero or default/null entries, the entropy is sub target-threshold and the method always proceeds to step 260 and/or 270 (in embodiments with the LFSR, the LFSR is "on"), resulting in reminders emitted at random intervals. The device's action during this initial period thus resembles that of a coach or teacher who has just acquired a new student. Later, after the time series buffer memory is filled with actual user activity time series data (typically several thousand steps, accrued over the previous 24 hours), if the entropy exceeds the target threshold then the method proceeds to step 255 (in embodiments with an LFSR, the LFSR is disabled) and reminders are suppressed. Again, this action closely mimics that of a coach or teacher who attentively, but "invisibly", monitors a student with whom s/he is already familiar and whose performance conforms to the training plan. Thus in some embodiments of the invention, a prolonged pattern of non-adherence generates a correspondingly prolonged period of intensive reminding, until the entropy of the "boxcar" buffer memory containing the steps-per-15-min time series once again ascends above the target threshold.

Reminding that is routinized, periodic, ongoing habitual interaction becomes boring or intrusive, and adherence rapidly declines. By contrast, this coach-like, time-limited, carefully targeted, entropy-triggered reminding pattern of haptic or other feedback achieves higher levels of adherence that are sustained over prolonged intervals. Such a reminding system and method can become a part of a comprehensive suite of strategic psychological support practices, to promote and effectively achieve health goals.

Example embodiments of the invention were evaluated on users and shown to be effective. Participants were instructed to wear a device embodiment of the invention during day time, except during bathing. Participants who did not manage to record 500 min/d of activity for three d were excluded from further analyses. Zero-activity periods of 10 minutes were interpreted as "not-worn" time intervals, and these periods were removed from the summation of activity. Weight loss over a 3-month period averaged 14% for overweight subjects.

With continuing reference to FIGS. 1A through 2, additional example embodiments include:

A computer-implemented method for accelerometry-based logging of ambulation and other physical activity utilizing sensor data acquisition and a data processing system, comprising: (a) determining the degree of variability of activity during ultradian time intervals, preferably less than 90 min and more preferably between 10 min and 30 min; and (b) conditionally and intermittently emitting a reminder signal in real-time, and involving one or more of: a haptic (tactile vibration) signal, sensible on the skin of the user in the area where the wearable monitoring device is affixed; an audible signal; and a supportive or affirmative textual or symbolic message—on a display that is part of the device itself, or on a mobile phone or other wireless communication device carried by the user.

In some embodiments of the computer-implemented method, a 24-hour buffer of stored accelerometry timeseries data is continuously characterized by a quantitative measure of variability, comprising a Shannon, Jeffreys, Laplace, Minimax, Tsallis, Chao-Shen, Dirichlet, Miller-Madow, James-Stein Shrinker, or Nemenman-Shafee-Bialek (NSB) entropy, or other measures of variability such as RMSSD or other measures such as are known to those practiced in the art. In some embodiments of the computer-implemented method, the calculation of the variability measure is performed at ultradian intervals, preferably less than 90 min and more preferably between 10 and 30 min.

In some embodiments of the computer-implemented method, each successive determination of low-entropy sedentariness within a specified time interval is checked against previous determinations by the method used from the types of methods listed above, and if two consecutive determinations are less than a target entropy threshold then that shall be used as a trigger to cause the generation of an electronic reminder to prompt the user to commence a bout of ambulatory activity or light exercise.

In some embodiments of the computer-implemented method, the user's physical activity (or lack thereof) subsequent to receiving an alert or reminder is ascertained and logged in the device's memory for subsequent analysis and personalization of future reminders. In some embodiments of the computer-implemented method, the reminder signal is emitted for not less than 10 seconds. In some embodiments of the computer-implemented method, the monitoring and analysis of activity variability and of compliance with the emitted reminders are implemented by periodically synchronizing a user worn monitoring device with data storage and software applications that are present on the user's laptop computer, on a web-based host service, or other computational resources.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

It will be understood that certain features and subcombinations are of utility and may be employed without reference to other features and subcombinations and are contemplated within the scope of the claims. Not all steps listed in the various figures need be carried out in the specific order described.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

What is claimed is:

1. Non-transitory computer-readable media having computer-executable instructions embodied thereon, that, when executed by one or more processors, implement a method of generating and providing adaptive activity reminders to a user, via a user device, for promoting positive activity patterns for the user, the method comprising:

receiving on a computing device a first set of user-motion information over a first time interval, the first set of user-motion information determined from one or more sensors positioned at one or more locations on the user, wherein the first set of user-motion information includes user-motion measurements obtained over the first time interval which correspond to a first ambulation for the user during the first time interval;

calculating a first entropy for an amount of variation in the first ambulation based on the user-motion measurements, wherein the first entropy is a quantitative measure of the amount of variation for the first ambulation for the user during the first time interval;
specifying a target entropy threshold amount of ambulation variation;
comparing, in a first comparison, the target entropy threshold to the first entropy of the first ambulation during the first time interval;
based on the first comparison, determining whether the first entropy of the first ambulation is less than the target entropy threshold;
when the first entropy of the first ambulation is less than the target entropy threshold, then generating a pseudorandom value;
based on the generated pseudorandom value, determining a pseudorandom interval; and
at the pseudorandom interval, generating an activity reminder and presenting the activity reminder by way of a user interface on the user device, wherein the presented activity reminder prompts the user to perform a physical activity that increases an entropy level of user activity.

2. The computer-readable media of claim 1, further comprising:
receiving a second set of user-motion information over a second time interval;
based on the received second set of user-motion information, calculating a second entropy for a second ambulation for the user during the second time interval; and
comparing, in a second comparison, the target entropy threshold to the second entropy for the second ambulation;
wherein the pseudorandom value is generated based on each of the first entropy level for the first ambulation and the second entropy level for the second ambulation being less than the target entropy threshold.

3. The computer-readable media of claim 2, wherein the first time interval immediately precedes the second time interval.

4. The computer-readable media of claim 1, wherein the pseudorandom value represents logically true or false, and wherein presenting the activity reminder comprises presenting the activity reminder when the pseudorandom value represents logically true, and not presenting the activity reminder when the pseudorandom value represents logically false.

5. The computer-readable media of claim 1, wherein the activity reminder comprises at least one of an audible alert, a haptic alert, a displayed message, a displayed visual indicator, or a text message.

6. The computer-readable media of claim 1, wherein the activity reminder comprises a report provided to a health care provider.

7. The computer-readable media of claim 1 further comprising:
responsive to a provided activity reminder, receiving a third set of user-motion information over a third time interval succeeding the first time interval;
based on the received third set of user-motion information, calculating a third entropy for a third ambulation for the user during the third time interval; and
storing the third entropy for the third ambulation for the user.

8. The computer-readable media of claim 5 wherein the activity reminder is provided for at least 10 seconds.

9. The computer-readable media of claim 1, wherein calculating the first entropy of the first ambulation comprises calculating one of Shannon, Jeffreys, Laplace, Minimax, Tsallis, Chao-Shen, Dirichlet, Miller-Madow, James-Stein Shrinker, or Nemenman-Shafee-Bialek (NSB) entropy, or RMSSD variability.

10. The computer-readable media of claim 2 wherein the first and second time intervals comprise ultradian time intervals between 10 and 30 minutes.

11. A monitoring device that provides adaptive activity reminders for promoting positive activity patterns for a user, comprising:
a user interface;
one or more computing devices that:
(1) receive a first set of user-motion information over a first time interval, the first set of user-motion information determined from one or more sensor circuits, wherein the first set of user-motion information includes user-motion measurements obtained over the first time interval which correspond to a first ambulation for the user during the first time interval;
(2) calculate a first entropy for a first activity pattern based on the user-motion measurements, wherein the first entropy is a quantitative measure of the amount of variation in a level of activity for the first activity pattern for the user during the first time interval;
(3) specify a target entropy threshold amount of variation;
(4) compare, in a first comparison, the target entropy threshold to the first entropy of the first activity pattern during the first time interval;
(5) based on the first comparison, determine whether the first entropy of the first activity pattern is less than the target entropy threshold;
(6) when the first entropy of the first activity pattern is less than the target entropy threshold, then generate a pseudorandom value;
(7) based on the generated pseudorandom value, determine a pseudorandom interval; and
(8) at the pseudorandom interval, generate an activity reminder and present the activity reminder by way of the user interface, wherein the presented activity reminder prompts the user to perform a physical activity associated with a positive activity pattern.

12. The monitoring device of claim 11, wherein the one or more computing devices further:
receive a second set of user-motion information over a second time interval;
based on the received second set of user-motion information, calculate a second entropy for a second activity pattern for the user during the second time interval; and
compare, in a second comparison, the target entropy threshold to the second entropy for the second activity pattern;
wherein the pseudorandom value is generated based on each of the first entropy for the first activity pattern and the second entropy for the second activity pattern being less than the target entropy threshold.

13. The monitoring device of claim 12, wherein the first time interval immediately precedes the second time interval.

14. The monitoring device of claim 11, wherein the pseudorandom value represents logically true or false, and wherein presenting the activity reminder comprises presenting the activity reminder when the pseudorandom value represents logically true, and not presenting the activity reminder when the pseudorandom value represents logically false.

15. The monitoring device of claim 11, wherein the activity reminder comprises at least one of an audible alert, a haptic alert, a displayed message, a displayed visual indicator, or a text message.

16. The monitoring device of claim 11, wherein the activity reminder comprises a report provided to a health care provider.

17. The monitoring device of claim 11 further comprising:
responsive to a provided activity reminder, receiving a third set of user-motion information over a third time interval succeeding the first time interval;
based on the received third set of user-motion information, calculating a third entropy for a third activity pattern for the user during the third time interval; and
storing the third entropy for the third activity pattern for the user.

18. The monitoring device of claim 15 wherein the activity reminder is provided for at least 10 seconds.

19. Non-transitory computer-readable media having computer-executable instructions embodied thereon, that, when executed by one or more processors, implement a method of generating and providing adaptive activity reminders to a user, via a user device, for promoting positive activity patterns for the user, the method comprising:
receiving on a computing device a first set of user-motion information over a first time interval, the first set of user-motion information determined from one or more sensors, wherein the first set of user-motion information includes user-motion measurements obtained over the first time interval which correspond to a first ambulation for the user during the first time interval;
calculating a first entropy for an amount of variation in the first ambulation based on the user-motion measurements, wherein the first entropy is a quantitative measure of the amount of variation for the first ambulation for the user during the first time interval;
specifying a target entropy threshold of ambulation variation;
comparing, in a first comparison, the target entropy threshold to the first entropy of the first ambulation during the first time interval;
based on the first comparison, determining whether the first entropy of the first ambulation is less than the target entropy threshold;
when the first entropy of the first ambulation is less than the target entropy threshold, then generating a pseudorandom value, wherein the pseudorandom variable is generated based as least in part on a linear feedback shift register;
based on the generated pseudorandom value, determining a pseudorandom interval; and
at the pseudorandom interval, generating an activity reminder and presenting the activity reminder by way of a user interface on the user device, wherein the presented activity reminder prompts the user to perform a physical activity associated with a positive activity pattern.

* * * * *

UNITED STATES PATENT AND TRADEMARK OFFICE
CERTIFICATE OF CORRECTION

PATENT NO. : 10,420,486 B1
APPLICATION NO. : 13/751961
DATED : September 24, 2019
INVENTOR(S) : Douglas S. McNair Page 1 of 1

It is certified that error appears in the above-identified patent and that said Letters Patent is hereby corrected as shown below:

In the Specification

Column 08, Line 18: Please remove "53" and replace with --S3--.
Column 12, Line 52: Please remove "(PGC)-Ialpha," and replace with --(PGC)-1 alpha--.
Column 12, Line 56: Please remove "PGC-Ialpha" and replace with --PGC-1 alpha--.
Column 12, Line 57: Please remove "PGC-Ialpha" and replace with --PGC-1 alpha--.
Column 12, Line 58: Please remove "PGC-Ialpha" and replace with --PGC-1 alpha--.
Column 12, Line 62: Please remove "PGC-Ialpha" and replace with --PGC-1 alpha--.
Column 12, Line 67: Please remove "PGC-Ialpha" and replace with --PGC-1 alpha--.
Column 13, Line 01: Please remove "PGC-Ialpha" and replace with --PGC-1 alpha--.
Column 13, Line 03: Please remove "PGC-Ialpha" and replace with --PGC-1 alpha--.
Column 13, Line 04: Please remove "PGC-Ialpha" and replace with --PGC-1 alpha--.
Column 13, Line 06: Please remove "PGC-Ialpha" and replace with --PGC-1 alpha--.
Column 13, Line 09: Please remove "PGC-Ialpha" and replace with --PGC-1 alpha--.
Column 13, Line 12: Please remove "PGC-Ialpha" and replace with --PGC-1 alpha--.
Column 19, Line 45: Please remove ""needs"" and replace with --"needs"--.
Column 19, Line 53: Please remove "I interval" and replace with --τ interval--.

In the Claims

Column 26, Line 19: Please remove "as least" and replace with --at least--.

Signed and Sealed this
Tenth Day of December, 2019

Andrei Iancu
*Director of the United States Patent and Trademark Office*